United States Patent
Yonce

(10) Patent No.: US 6,741,886 B2
(45) Date of Patent: May 25, 2004

(54) ECG SYSTEM WITH MINUTE VENTILATION DETECTOR

(75) Inventor: David J. Yonce, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 411 days.

(21) Appl. No.: 10/037,773

(22) Filed: Oct. 25, 2001

(65) Prior Publication Data

US 2003/0083707 A1 May 1, 2003

(51) Int. Cl.⁷ .................................................. A61B 5/04
(52) U.S. Cl. ........................................................ 600/510
(58) Field of Search ................................ 600/508, 509, 600/510, 529, 534, 536; 607/5, 9, 20, 27, 28, 29

(56) References Cited

U.S. PATENT DOCUMENTS

| | | | |
|---|---|---|---|
| 3,779,237 A | 12/1973 | Goelte et al. | |
| 3,871,360 A | 3/1975 | Van Horn et al. | |
| 4,539,999 A | 9/1985 | Mans | |
| 4,664,116 A | 5/1987 | Shaya et al. | |
| 5,137,019 A | 8/1992 | Pederson et al. | |
| 5,318,597 A | 6/1994 | Hauck et al. | |
| 5,331,966 A | 7/1994 | Bennett et al. | |
| 5,448,997 A | 9/1995 | Kruse et al. | |
| 6,141,592 A | 10/2000 | Pauly | |
| 6,597,942 B1 * | 7/2003 | Yonce | 600/509 |
| 2003/0083584 A1 * | 5/2003 | Yonce | 600/509 |

* cited by examiner

*Primary Examiner*—George Manuel
(74) *Attorney, Agent, or Firm*—Thomas J. Nikolai; Nikolai & Mersereau, P.A.

(57) ABSTRACT

The ability of an ecg apparatus to detect and display pacing pulses from the surface electrodes on a patient in whom a minute ventilation-based rate adaptive pacemaker is implanted is improved by providing the ecg apparatus with a minute ventilation detection circuit capable of indicating the time of occurrence and repetition rate of bursts of AC carrier signals which the implanted pacemaker generates in deriving a minute ventilation related control signal for the implanted pacemaker. In addition to improving the ability of the ecg system to detect and record paced events, the incorporation of the MV detection into the ecg system accommodates leads-off detection by coordinating the generation of the leads-off drive signal with the MV carrier signal generated by the implanted pacer.

18 Claims, 6 Drawing Sheets

ECG SYSTEM WITH MINUTE VENTILATION DETECTOR

BACKGROUND OF THE INVENTION

I. Field of the Invention

This invention relates generally to electrocardiograph apparatus and/or programming equipment for cardiac rhythm management devices (CRMD) employed to monitor and record cardiac depolarization and repolarization signals, and more particularly to the incorporation into such equipment of a minute ventilation detector for providing an indication of when an implanted MV (minute ventilation-based) rate adaptive CRMD is generating a AC carrier signal used in deriving a minute ventilation related control signal for the implanted device.

II. Discussion of the Prior Art

One type of rate adaptive cardiac pacemaker on the market today uses a patient's minute ventilation as a rate control parameter. In such rate adaptive pacemakers/defibrillators, transthoracic impedance is measured by applying an AC carrier signal of a predetermined frequency, typically about 30 KHz, from an oscillator between an electrode carried by a pacing lead disposed in the heart and an electrode on the pacemaker can that is usually located in a surgically formed pocket beneath the pectoral muscle in the patient's chest. This AC carrier signal is modulated by respiratory activity (inspiration and expiration) and a rate control signal is derived by demodulating the carrier. The Hauck et al. U.S. Pat. No. 5,318,597 may be referred to for additional disclosure of the construction and mode of operation of MV based rate adaptive pacemakers.

While the frequency of the AC carrier is generally outside of the bandwidth of most physiologic signals, the amplitude of the carrier frequently dominates electrocardiograph input signals and can interfere with the detection of pacing pulses put out by the implanted device. It is also true that electrocardiograph equipment, especially those incorporating leads-off indication, can adversely affect operation of an implanted minute ventilation-based rate adaptive pacemaker, causing erroneously high pacing rates.

The need, therefore, exists for a way to better render electrocardiograph and patient programmers used with CRMDs compatible with minute ventilation-based rate adaptive pacemakers.

SUMMARY OF THE INVENTION

A solution to the foregoing undesired interaction resides in providing an ecg recorder for detecting and displaying cardiac signals picked up on a plurality of skin-contacting surface electrodes disposed on a patient at predetermined body locations in whom a rate-adaptive cardiac rhythm management device is implanted with a MV detector. The cardiac rhythm management device can be of a type that may have minute ventilation as a control parameter for the rate at which the device produces pacing pulses. The minute ventilation based rate adaptive device includes a means for impressing a sub-threshold carrier signal of a given high frequency in timed bursts of a predetermined repetition rate between a first electrode disposed within a patient's thoracic cavity and a reference electrode. The MV detection circuit in the ecg recorder or CRMD programmer is connected to receive signals picked up by pairs of the plurality of surface electrodes, such signals including cardiac signal components, pacing pulse components, noise components and components due to the attenuating current carrier. The minute ventilation detection circuit indicates the time of occurrence of the components due to the carrier signal.

Without limitation, the minute ventilation detection circuit may comprise a matched filter that is coupled to receive the signals picked up by the pairs of surface electrodes along with a template comprising signals of the given high frequency, or, if in the digital domain, approximate filter coefficients. A comparator is coupled to receive the output of the matched filter and a reference signal. The comparator produces an output indicating the time of occurrence of the components due to the carrier signal when the output of the matched filter exceeds the reference signal.

DESCRIPTION OF THE DRAWINGS

Further features, applications and advantages of the present invention will become apparent to those skilled in the art from the following detailed description of the preferred embodiment, especially when considered in conjunction with the accompanying drawings in which.

DESCRIPTION OF THE PREFERRED EMBODIMENTS

Figure 1:
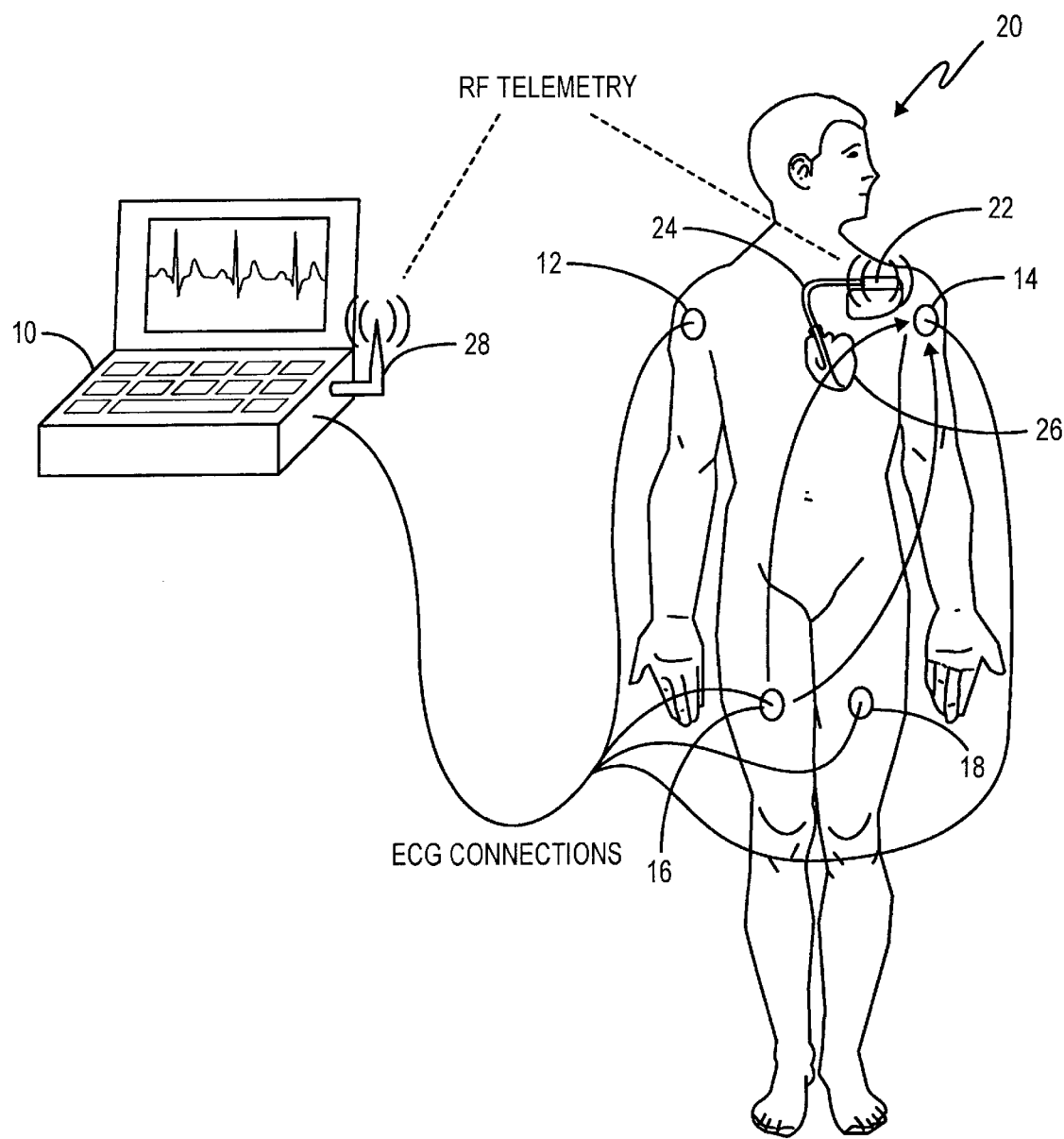
FIG. 1 is a general block diagram of the system in which the present invention finds use.

Referring first to FIG. 1, there is shown an ecg recorder 10 which may be embodied in a programmer/monitor used with implantable cardiac rhythm management devices. It is shown as having a plurality of skin contacting electrodes, including a right arm (RA) electrode 12, a left arm (LA) electrode 14, a right leg (RL) electrode 16 and a left leg (LL) electrode 18 on a patient 20. The patient is also shown as having a minute ventilation rate adaptive cardiac pacemaker 22 implanted and connected by conventional pacing/sensing leads 24 to electrodes disposed within the heart 26. The ecg recorder 10 is shown as having a telemetry antenna 28 which, when positioned proximate the implanted device 22, allows two-way communication via a telemetry link. The communications link may also comprise the standard magnetic coil telemetry wand commonly used to exchange information between an external programmer and an implanted medical device.

Figure 2:
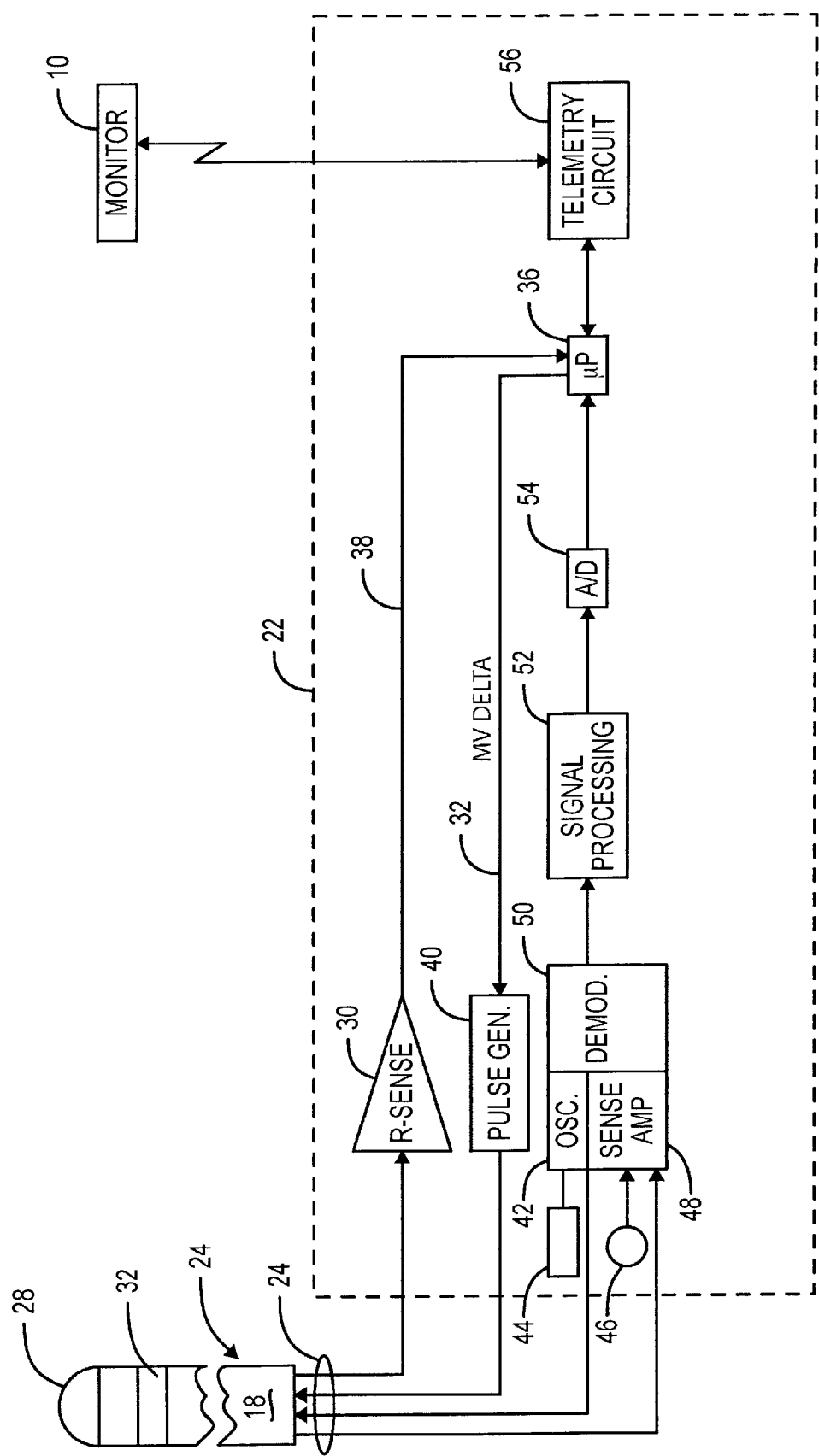
FIG. 2 is a block diagram of an implantable minute ventilation based rate adaptive pacemaker.

Referring next to FIG. 2, there is illustrated a block diagram of the implantable device 22. It is seen to include a sense amplifier 30 connected via the lead 24 to electrodes 32 and 34. Cardiac depolarization signals (R-waves) are amplified and applied to a microprocessor 36, via a conductor 38. The microprocessor is programmed to control a pulse generator 40 causing it to emit cardiac stimulating pulses there applied to the heart, via the lead 24.

In order to develop a pacer rate control signal based upon the patient's minute ventilation, the implantable device 22 includes an oscillator 42 capable of producing timed bursts of relatively high frequency energy which are applied via an electrode 44 placed on or in the heart. This carrier signal is subject to modulation caused by inspiratory and expiratory activity and the resulting modulated carrier signal is picked up by an electrode 46 disposed on the implanted CRMD's housing and delivered to a sense amplifier 48. The output from the sense amplifier is demodulated by demodulator circuit 50 such that the modulating envelope is a measure of transthoracic impedance vs. time. This demodulation envelope is signal processed at 52 and converted to a digital format by A/D converter 54 and fed as an input to the microprocessor 36. Telemetry circuit 56, which is incorporated into the implantable unit 22, allows two-way communication with the external monitor/programmer 10.

Those wishing additional information on the design and operation of MV-based rate adaptive pacemakers may refer to the aforereferenced Hauck et al. '597 patent and the Pederson et al. U.S. Pat. No. 5,137,019, both of which are hereby incorporated by reference as if fully set forth herein.

Figure 3:
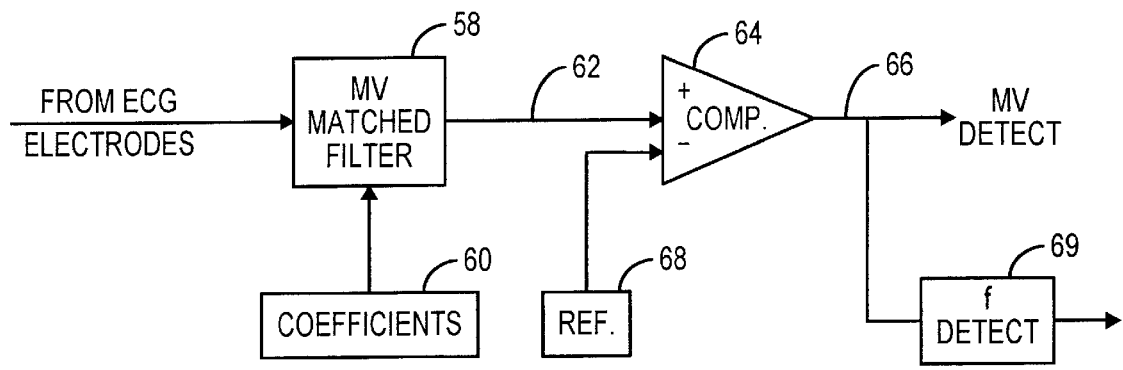
FIG. 3 is a block diagram of the minute ventilation detection circuit embodied in the ecg recorder of the present invention.

Turning then to FIG. 3, there is shown a block diagram of the MV detection circuit incorporated into the ECG recorder/CRMD programmer module 10 of FIG. 1. It includes a matched filter 58 having first inputs coupled to receive the signals picked up by the body contacting electrodes 12, 14, 16 and 18 along with a template input 60. The template may be an analog signal of a predetermined morphology or any filter coefficients for a FIR digital filter. The matched filter 58 may be any one of a number of known devices operative to produce an output on line 62 when input signals to the matched filter correspond to the template 60. The matched filter output on line 62 is applied as an input to a comparator circuit 64 which operates to produce a high output on line 66 when the input to the comparator exceeds a predetermined reference value 68. Those skilled in the art will appreciate that the MV detect circuit of FIG. 3 can be implemented in either the analog or the digital domain.

In use, the template 60 will be a signal of substantially the same frequency as the AC carrier produced by oscillator 42 of the implanted CRMD 22. Thus, at the time instances when the MV carrier bursts are picked up by the ECG electrodes, the MV detect circuit of FIG. 3 will produce an output in substantial time coincidence thereof.

Most MV-based rate adaptive pacemakers output the 30 KHz carrier signal in timed bursts, for example, every 47.04 ms. This rate information may be used to help distinguish true MV signals from noise. Thus, if the detector circuit of FIG. 3 produces a MV detection at rates other than integer multiples of 47.04 seconds, then it is known that noise is corrupting the detector and producing false MV indications. A frequency detector 69 is coupled to receive the signals from comparator 64 and functions to measure the repetition rate of the MV carrier bursts.

Figure 4:
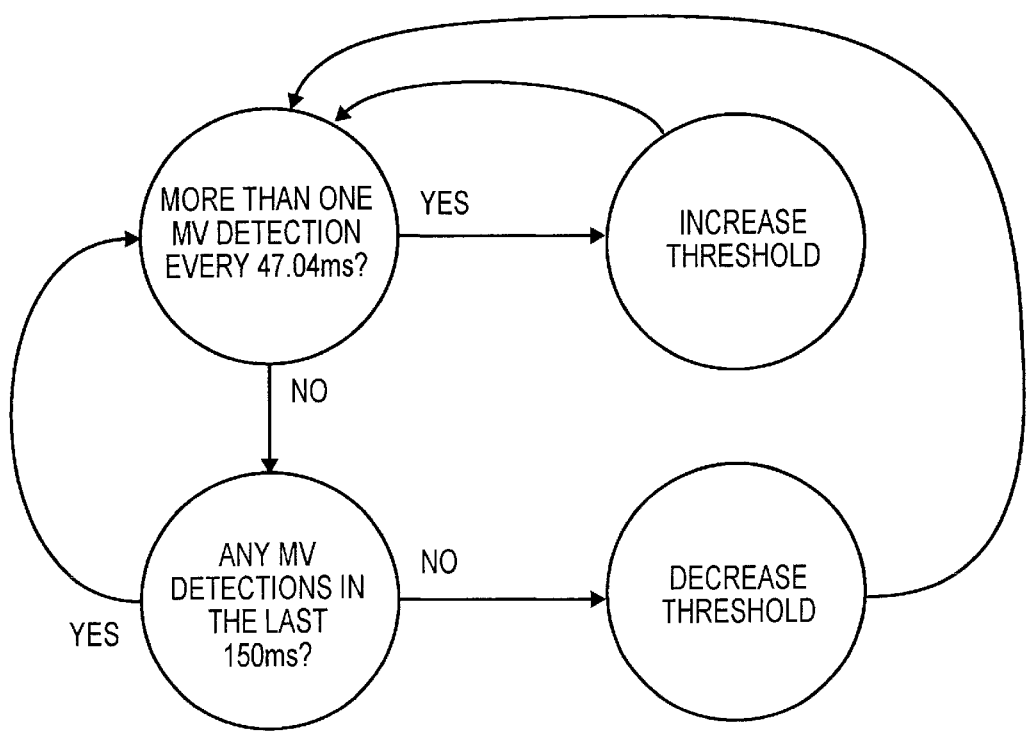
FIG. 4 depicts a state machine for adaptively adjusting the threshold level for the comparator of the minute ventilation detector circuit of FIG. 2.

A further feature of the present invention is to utilize the rate information to dynamically change the reference threshold 68 of the comparator 64 to optimize noise rejection. For example, if the frequency detector 69 indicates more than one MV detection every 47.04 ms, then the reference threshold is made to increase until the number of detections decreases to the appropriate rate. In this manner, the system dynamically sets the threshold level above the noise floor. FIG. 4 is a state machine configured to adjust the threshold level in the manner just described.

Figure 5:
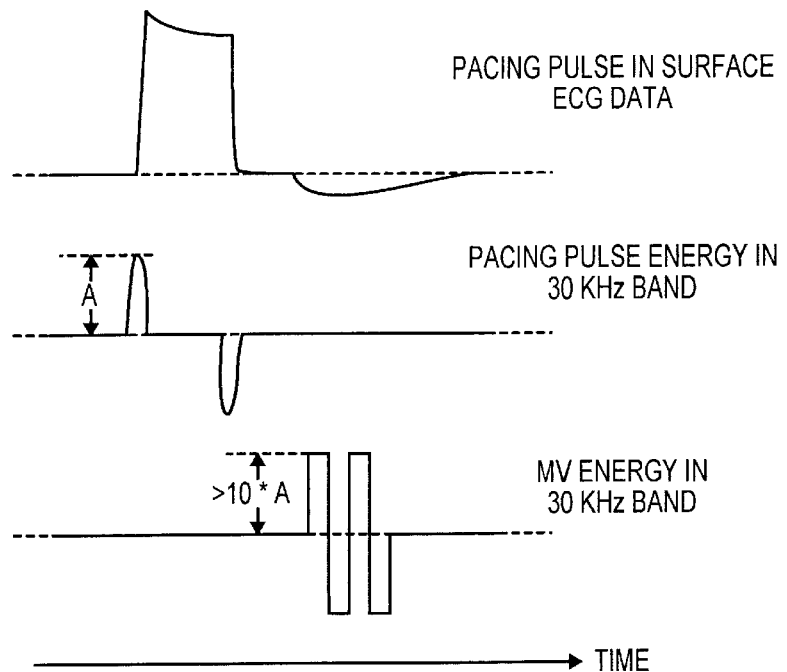
FIG. 5 are exemplary waveforms helpful in explaining operation of the minute ventilation detector in distinguishing pacing pulses from noise and an AC carrier signal.
Figure 6:
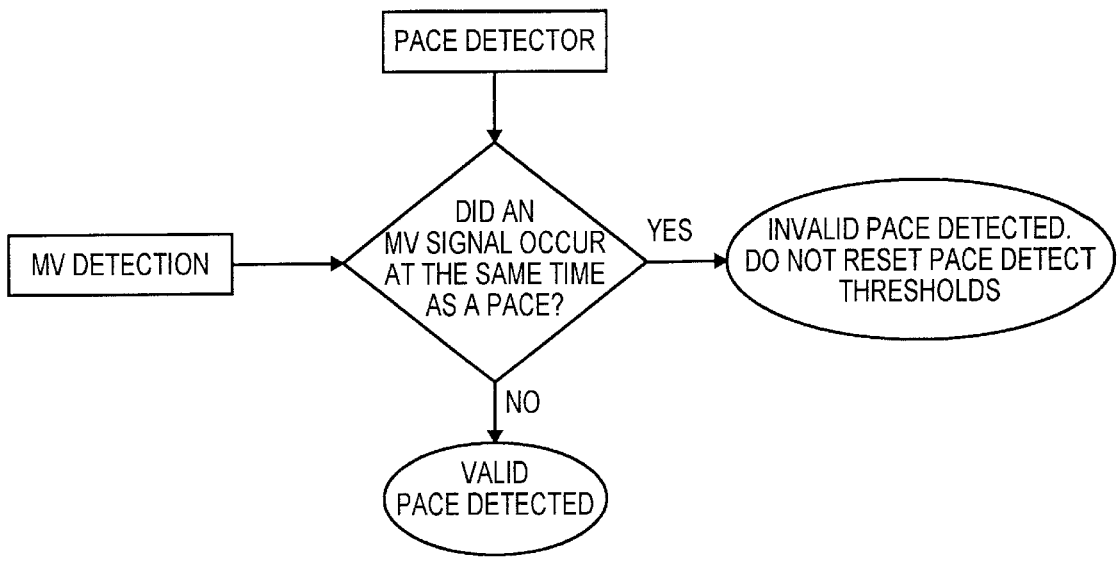
FIG. 6 is a software flow diagram of an improved pace detection algorithm taking advantage of the minute ventilation detector.

Having explained the functioning of the MV detect circuit to identify the time of occurrence of high frequency carrier bursts from the implanted pacemaker device, the utility thereof in improving the ability of the ECG recorder to detect pacing pulses within the surface ECG data will next be explained. As is explained in our pending application Ser. No. 09/516,533, filed Mar. 1, 2000, entitled "System and Method for Detection of Pacing Pulses Within ECG Signals", which is also incorporated by reference, signals in the 30 KHz band can interfere with the detection of pacing pulses picked up by the body contacting surface electrodes, especially when edge detection is employed to help discriminate pacing pulses from background noise. To distinguish the pacing edges, incoming ECG signals are filtered at frequencies around 1 KHz and about 30 KHz. Because the minute ventilation carrier frequency is close to this range, the MV signals tend to dominate in this band. FIG. 5 illustrates the shape of a pacing pulse and MV signals within ECG data. Because MV signals are often an order of magnitude greater than pacing signatures, the MV signals can inappropriately increase dynamic thresholds of pace detect algorithms if not properly detected as noise. To help discern MV signals as noise during pace detection, the output of the MV detector of FIG. 3 is incorporated into the pacing detector functionality. FIG. 6 is a simplified software flow diagram of an improved pacing detection algorithm which utilizes the output of a pace detection algorithm, such as described in the aforementioned application Ser. No. 09/516,533, along with the output of the MV detector. As is reflected in FIG. 6, once a possible pace is recognized, the system checks the output of the MV detector to verify that no MV detections occurred at the same time as the pace event. If so, a valid pace is declared. On the other hand, if a MV signal is sensed at the same time as the pace, the pace detect algorithm inadvertently detected the MV signal as a pace event. In this situation, the possible pace is declared invalid and any pace detect noise thresholds are not adjusted. In this manner, the additional MV detection criteria improves the rejection of noise from the pace detection algorithm and prevents a seeding of the pace detection thresholds with a grossly large value.

Figure 7:
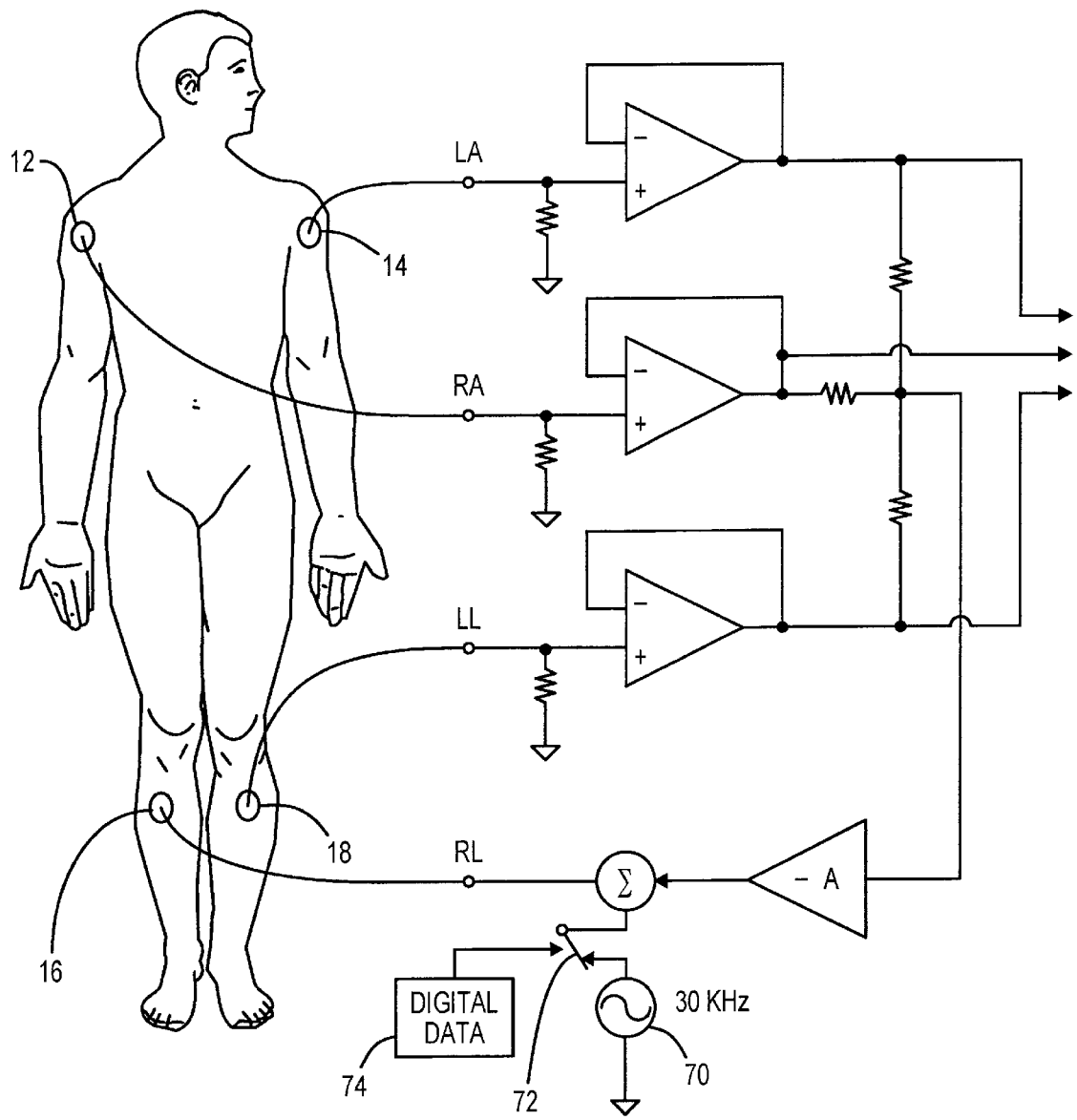
FIG. 7 illustrates the configuration of a "leads-off indicator" employed in ecg equipment.

In my copending patent application Ser. No. 09/639,037, filed Aug. 15, 2000, I point out that many ECG machines incorporate a "lead-off indicator" to help identify a high impedance ECG electrode patch. By providing such an indicator, a medical professional is able to quickly locate the source of a noisy signal and take appropriate steps to secure the lead patch to the patient's skin. It is further explained that most conventional leads-off indicators use simple impedance measurements to determine whether an electrode is attached to the patient. Typically, the ECG machine has an AC signal source 70 that is adapted to apply a relatively high frequency drive signal, again in the 30 KHz range, to the patient through electrode 16 affixed to the patient's right leg as illustrated in FIG. 7. The ECG then measures this signal through the other input electrodes 12, 14 and 18 to determine whether the electrodes are properly attached by comparing the amplitude of the transduced 30 KHz signal to a predetermined reference. When ECG machines with such prior art style leads-off indicators are used with pacemaker patients having a MV-based rate adaptive pacemaker, the leads-off indicator can drive the pacing rate of the pulse generator up to its programmed upper-rate limit.

By incorporating the MV detector of the present invention into the ECG recorder, it can be used in conjunction with the leads-off indicator to help prevent this unwanted interaction. Using the output of the frequency detector 69 of the MV detector of FIG. 3 to first recognize the characteristic repetition rate of the MV carrier pulse, the 30 KHz leads-off indicator signal from source 70 is then interlaced in time, operating between the MV carrier bursts produced by the oscillator 42 of the implanted CRMD. The waveforms of FIG. 8 illustrate how the minute ventilation signals from an implanted rate adaptive pacemaker are detected and used to predict the time of occurrence of a succeeding burst allowing synchronization of the generation of the leads-off signal in the ECG recorder apparatus so that the leads-off signal occurs between bursts of the MV carrier signal and thereby prevents interaction with the MV sensor 48 and demodulator 50 by operating in the time intervals between expected MV sensing activity within the implanted device.

Figure 8:
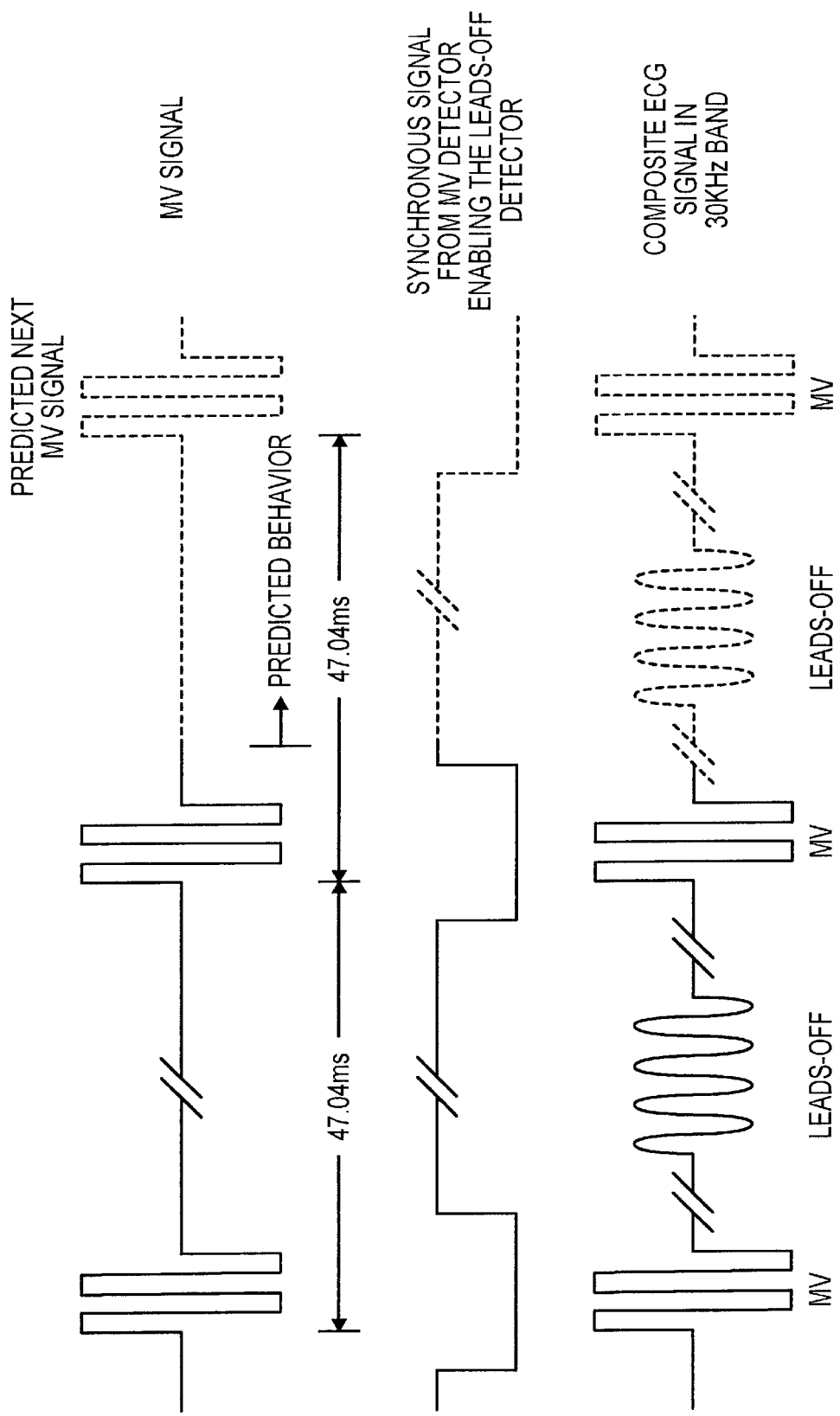
FIG. 8 are waveforms showing a time relationship of pacemaker minute ventilation carrier signals to the ecg leads-off signals.

With continued reference to FIGS. 7 and 8, the incorporation of the minute ventilation detector of FIG. 3 into the CRMD programmer/monitor 10 will allow communication between the external device and the implanted device. By moving the switch 72 from the position shown when used for leads-off indication to its position connecting the digital data source 74 and by configuring the telemetry circuit 56 (FIG. 2) so that its sensing amplifier will detect the data stream sent between the RL reference electrode 16 and the other ECG input electrodes 12, 14 and 18, the MV detector can again establish a time intervals between detected bursts of the MV carrier in which the ECG apparatus transmits the digital data stream. Thus, in the timing diagram of FIG. 8, the digital data stream would be transmitted in place of the 30 KHz leads-off drive signal in the interval between MV carrier bursts once the MV detector and the frequency counter 69 have predicted the time of occurrence of the next succeeding burst.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. An ecg recorder for detecting and displaying cardiac signals picked up on a plurality of skin contacting surface electrodes disposed on a patient at predetermined body locations in whom a rate-adaptive cardiac rhythm management device is implanted, the cardiac rhythm management device being of the type having minute ventilation as a control parameter for the rate at which the device produces pacing pulses, the device having a means for impressing a carrier signal of a given frequency in timed bursts of a predetermined repetition rate between a first electrode disposed within the patient's thoracic cavity and a reference electrode, comprising:
   (a) a minute ventilation detection circuit in the ecg recorder connected to receive signals picked up by pairs of said surface electrodes, the signals picked up by the pairs of said surface electrodes including cardiac signal components, pacing pulse components, noise components and components due to said carrier, said minute ventilation detection circuit indicating the time of occurrence of the components due to said carrier signal.

2. The ecg recorder of claim 1 wherein the minute ventilation detection circuit comprises:
   (a) a matched filter coupled to receive said signals picked up by the pairs of surface electrodes, along with signals of said given frequency and producing an output; and
   (b) a comparator coupled to receive the output of the matched filter, along with a reference signal, the comparator producing an output indicating the time of occurrence of the components due to the carrier signal when the output of the matched filter exceeds the reference signal.

3. The ecg recorder of claim 2 and further including:
   (a) a frequency detector coupled to the minute ventilation detection circuit for monitoring the repetition rate of said timed bursts; and
   (b) a reference signal adjustment device for varying the reference signal in response to an output from the frequency detector.

4. The ecg recorder of claim 3 wherein the reference signal adjustment device is operative to increase the reference signal when timed bursts occur at a repetition rate greater than the predetermined repetition rate and to decrease the reference signal when the timed bursts occur at a repetition rate less than the predetermined repetition rate.

5. An ecg recorder for detecting and displaying cardiac signals picked up on a plurality of skin contacting surface electrodes disposed on a patient at predetermined body locations in whom a rate-adaptive cardiac rhythm management device is implanted, the cardiac rhythm management device being of the type having minute ventilation as a control parameter for the rate at which the device produces pacing pulses, the device having a means for impressing a carrier signal of a given frequency in timed bursts of a predetermined repetition rate between a first electrode disposed within the patient's thoracic cavity and a reference electrode, comprising:
   (a) a pacing pulse detection apparatus in the ecg recorder connected to receive signals picked up by pairs of said surface electrodes, the signals picked up by the pairs of said surface electrodes including cardiac signal components, pacing pulse components, noise components and components due to said carrier, the pacing pulse detection apparatus being operative to compare energy present in a predetermined frequency band to a dynamic threshold whose value is based upon an amplitude of a preceding pacing pulse;
   (b) a minute ventilation detection apparatus in the ecg recorder connected to receive said signals picked up by said pair of surface electrodes and operative to indicate the time of occurrence of the components due to said carrier signal; and
   (c) means responsive to detection of a pacing pulse by the pacing pulse detection apparatus at the time of occurrence of the components due to said carrier signal as detected by the minute ventilation detection apparatus for inhibiting any change in the dynamic threshold.

6. The ecg recorder of claim 5 wherein the minute ventilation detection circuit comprises:
   (a) a matched filter coupled to receive said signals picked up by the pairs of surface electrodes, along with signals of said given frequency and producing an output; and
   (b) a comparator coupled to receive the output of the matched filter, along with a reference signal, the comparator producing an output indicating the time of occurrence of the components due to the carrier signal when the output of the matched filter exceeds the reference signal.

7. The ecg recorder of claim 6 and further including:
(a) a frequency detector coupled to the minute ventilation detection circuit for monitoring the repetition rate of said timed bursts; and
(b) a reference signal adjustment device for varying the reference signal in response to an output from the frequency detector.

8. The ecg recorder of claim 7 wherein the reference signal adjustment device is operative to increase the reference signal when timed bursts occur at a repetition rate greater than the predetermined repetition rate and to decrease the reference signal when the timed bursts occur at a repetition rate less than the predetermined repetition rate.

9. An ecg recorder for detecting and displaying cardiac signals picked up on a plurality of surface electrodes disposed on a patient at predetermined body locations in whom a rate-adaptive cardiac rhythm management device is implanted, the ecg recorder intermittently applying an AC signal to one of said plurality of surface electrodes to determine the state of conduction between the other of said plurality of surface electrodes and the patient's skin, the cardiac rhythm management device being of the type having minute ventilation as a control parameter for the rate at which the device produces pacing pulses, the device having a means impressing a carrier signal of a given frequency close to said AC signal in timed bursts of a predetermined repetition rate between a first electrode in the patient's thoracic cavity and a reference electrode, comprising:
(a) a minute ventilation detection apparatus in the ecg recorder connected to receive signals picked up by pairs of said surface electrodes, the signals picked up by the pairs of said surface electrodes, including cardiac signal components, pacing pulse components, noise components, components due to said carrier signal and operative to indicate the time of occurrence of the components due to said carrier signal; and
(b) control means responsive to the minute ventilation detection apparatus for causing the AC signal applied to said one of said plurality of surface electrodes to be interlaced in time with said carrier signal.

10. The ecg recorder of claim 9 wherein the minute ventilation detection circuit comprises:
(a) a matched filter coupled to receive said signals picked up by the pairs of surface electrodes, along with signals of said given frequency and producing an output; and
(b) a comparator coupled to receive the output of the matched filter, along with a reference signal, the comparator producing an output indicating the time of occurrence of the components due to the carrier signal when the output of the matched filter exceeds the reference signal.

11. The ecg recorder of claim 10 and further including:
(a) a frequency detector coupled to the minute ventilation detection circuit for monitoring the repetition rate of said timed bursts; and
(b) a reference signal adjustment device for varying the reference signal in response to an output from the frequency detector.

12. The ecg recorder of claim 11 wherein the reference signal adjustment device is operative to increase the reference signal when timed bursts occur at a repetition rate greater than the predetermined repetition rate and to decrease the reference signal when the timed bursts occur at a repetition rate less than the predetermined repetition rate.

13. An ecg recorder for detecting and displaying cardiac signals picked up on a plurality of skin contacting surface electrodes disposed on a patient at predetermined body locations in whom a rate-adaptive cardiac rhythm management device is implanted, the cardiac rhythm management device being of the type having minute ventilation as a control parameter for the rate at which the device produces pacing pulses, the device having a means for impressing a carrier signal of a given frequency in timed bursts of a predetermined repetition rate between a first electrode disposed within the patient's thoracic cavity and a reference electrode, comprising:
(a) a minute ventilation detection circuit in the ecg recorder connected to receive signals picked up by pairs of said surface electrodes, the signals picked up by the pairs of said surface electrodes including cardiac signal components, pacing pulse components, noise components and components due to said carrier, said minute ventilation detection circuit indicating the time of occurrence of the components due to said carrier signal; and
(b) a communication link in the ecg recorder response to the minute ventilation detection circuit for transmitting data to and receiving data from the implanted cardiac rhythm management device only during time intervals between occurrences of components due to said carrier signal.

14. The ecg recorder of claim 13 wherein the minute ventilation detection circuit comprises:
(a) a matched filter coupled to receive said signals picked up by the pairs of surface electrodes, along with signals of said given frequency and producing an output; and
(b) a comparator coupled to receive the output of the matched filter, along with a reference signal, the comparator producing an output indicating the time of occurrence of the components due to the carrier signal when the output of the matched filter exceeds the reference signal.

15. The ecg recorder of claim 14 and further including:
(a) a frequency detector coupled to the minute ventilation detection circuit for monitoring the repetition rate of said timed bursts; and
(b) a reference signal adjustment device for varying the reference signal in response to an output from the frequency detector.

16. The ecg recorder of claim 15 wherein the reference signal adjustment device is operative to increase the reference signal when timed bursts occur at a repetition rate greater than the predetermined repetition rate and to decrease the reference signal when the timed bursts occur at a repetition rate less than the predetermined repetition rate.

17. A method of operating an ECG recorder/programmer on a non-interfering basis with a minute ventilation based rate-adaptive pacemaker implanted in a patient, the pacemaker producing timed bursts of AC carrier signal, comprising the steps of:
(a) providing the ECG recorder/programmer having a plurality of surface electrodes with a minute ventilation detection circuit coupled to said surface electrodes for detecting the time of occurrence of said timed bursts of AC carrier signal;
(b) determining from the time of occurrence of the timed bursts of AC carrier signal a predicted time interval between successive bursts of the timed bursts of AC carrier signal; and
(c) telemetering information between the ECG recorder/programmer and the implanted pacemaker in the predicted time interval.

18. A method of operating an ECG recorder/programmer of a type having a leads-off indicator in which an AC signal of a predetermined frequency is periodically applied to a patient's body at a first ECG surface electrode location and picked up by ECG surface electrodes at a second location on a non-interfering basis with a minute ventilation based rate adaptive pacemaker implanted in the patient, the pacemaker producing timed bursts of AC carrier signal, comprising the steps of:

(a) providing the ECG recorder/programmer with a minute ventilation detection circuit that is coupled to said surface electrodes for detecting the time of occurrence of said timed bursts of AC carrier signal;

(b) determining from the time of occurrence of the timed bursts of AC carrier signal a predicted time interval between successive bursts of the timed bursts of AC carrier signal; and (c) generating the AC signal of a predetermined frequency within the predicted time interval.

* * * * *